United States Patent
Denu et al.

(10) Patent No.: US 7,358,092 B2
(45) Date of Patent: Apr. 15, 2008

(54) METHOD FOR THE DETERMINATION OF 25-HYDROXYCHOLECALCIFEROL IN FEED

(75) Inventors: Laurent Denu, Fillage-Neuf (FR); Richard Goessl, Grenzach-Wyhlen (DE); Peter Hofmann, Weil-Haltingen (DE)

(73) Assignee: DSM IP Assets B.V., TE Heerlen (NL)

( * ) Notice: Subject to any disclaimer, the term of this patent is extended or adjusted under 35 U.S.C. 154(b) by 43 days.

(21) Appl. No.: 10/581,789

(22) PCT Filed: Nov. 26, 2004

(86) PCT No.: PCT/EP2004/013427

§ 371 (c)(1),
(2), (4) Date: Jun. 6, 2006

(87) PCT Pub. No.: WO2005/059565

PCT Pub. Date: Jun. 30, 2005

(65) Prior Publication Data

US 2007/0117209 A1   May 24, 2007

(30) Foreign Application Priority Data

Dec. 9, 2003   (EP) .................................. 03028321

(51) Int. Cl.
*G01N 33/82* (2006.01)
*G01N 30/02* (2006.01)

(52) U.S. Cl. .................. 436/71; 436/20; 436/161; 436/173; 436/174; 436/177; 436/178; 210/656

(58) Field of Classification Search .................. 436/20, 436/71, 161, 173, 174, 177, 178; 210/656
See application file for complete search history.

(56) References Cited

U.S. PATENT DOCUMENTS

| 3,585,221 | A | * | 6/1971 | Luca | 552/653 |
| 5,316,770 | A | * | 5/1994 | Edwards, Jr. | 424/442 |
| 5,695,794 | A | * | 12/1997 | Stark et al. | 426/2 |
| 6,248,374 | B1 | * | 6/2001 | Murray et al. | 426/72 |
| 2006/0094125 | A1 | * | 5/2006 | Singh et al. | 436/127 |
| 2006/0228808 | A1 | * | 10/2006 | Clarke et al. | 436/173 |
| 2006/0228809 | A1 | * | 10/2006 | Clarke et al. | 436/173 |
| 2007/0082089 | A1 | * | 4/2007 | Krammer et al. | 426/72 |

OTHER PUBLICATIONS

Holmberg et al, "Determination of 25-hydroxyvitamin D3 in serum by high performance liquid chromatography and isotope dilution—mass spectrometry", Scandinavian Journal of Clinical and Laboratory Investigation, vol. 44, No. 4, 1984, pp. 275-282.

(Continued)

*Primary Examiner*—Maureen M. Wallenhorst
(74) *Attorney, Agent, or Firm*—Nixon & Vanderhye P.C.

(57) ABSTRACT

A method for quantitative determination of 25-hydroxycholecalciferol in feed is described. The method includes the steps of adding a defined amount of an internal standard which has a mass different from 25-hydroxycholecalciferol and a polarity similar to that compound, e.g., 26,27-hexadeutero-25-hydroxycholecalciferol, to an aqueous dispersion of the feed, extracting the aqueous dispersion with tert.butyl methyl ether and further processing the extract by HPLC and mass spectrometry as described in the specification.

8 Claims, 4 Drawing Sheets

OTHER PUBLICATIONS

Castro et al, "Determination of vitamin D3 metabolites: state-of-the-art and trends", Journal of Pharmaceutical and Biomedical Analysis, vol. 20, No. 1-2, Jun. 1999. pp. 1-17.

Rychener et al, "A Simplified and Improved Determination of Vitamin D in Fat, Oil and Margarine by HPLC", Mitteilungen Aus Dem Gebiete Der Lebensmitteluntersuchung UND Hygiene, vol. 76, No. 1, 1985, pp. 112-124.

Heudi et al, "Simultaneous quantification of Vitamins A, D3 and # in fortified infant formulae by liquid chromatography-mass spectrometry", Journal of Chromatography, Elsevier Science Publishers B.V. Amsterdam, NL. vol. 1022, No. 1-2, Jan. 2, 2004, pp. 115-123.

International Search Report.

* cited by examiner

METHOD FOR THE DETERMINATION OF 25-HYDROXYCHOLECALCIFEROL IN FEED

This application is the U.S. national phase of international application PCT/EP2004/013427 filed 26 Nov. 2004 which designated the U.S. and claims benefit of EP 03028321.2, dated 9 Dec. 2003, the entire content of which is hereby incorporated by reference.

The present invention relates to a method for the quantitative determination of 25-hydroxycholecalciferol (25-hydroxyvitamin $D_3$) in animal feed.

BACKGROUND OF THE INVENTION

25-Hydroxy-cholecalciferol is used as an additive to animal feed and is available as Hy-DTM (ROCHE VITAMINS AG, Basel, Switzerland) to improve the health status of animals such as livestock and pets. In view of its physiological potency and the narrow therapeutic window dosaging of the compound is critical and therefore, reliable analytical means are required to monitor the amount of the compound in feed and its uniform distribution therein. Various methods for the quantitative determination of 25-hydroxycholecalciferol in plasma have been described which are based on immunoassays, see WO 99/67211 or on HPLC/mass spectrometry using derivatives or isotopes as internal standards, see Biological & Pharmaceutical Bulletin (2001), 24(7), 738-743. However, these known methods are not satisfying when applied to the analysis of feed samples.

As all the old methods show it is difficult to analyse 25-hydroxycholecalciferol in feed samples due to the presence of big quantities of solid chemical and biological substances, whereas plasma or serum consist mainly of water. Two types of methods are available. A physicochemical method using HPLC and UV detection and an immunochemical method using HPLC for sample clean-up and radio-labeled immunoreagents, see Bruce. W. Hollis, Calcif. Tissue Int. (1996) 58:4-5. The other method, is also laborious and contains an analytical step, which uses radioactive material for the quantification. This method consists of the addition of $^3$H-25-hydroxycholecalciferol as internal standard, extraction with methanol, sample clean-up on reversed-phase SEP-PAK cartridges, further clean-up on normal-phase SEP-PAK cartridges, further clean-up on normal-phase HPLC and final intrinsic analytical reversed-phase HPLC. The overall recovery is determined by scintillation counting of the $^3$H-25-hydroxycholecalciferol. Quantification is done by external calibration and UV detection at 264 nm. The sample clean-up procedure is so laborious because the final quantification is done by UV. Such a complicated purification of the extract requires a determination of the recovery which is done using radio-labeled 25-hydroxycholecalciferol. Both methods are cumbersome, with many poor performance characteristics and reproducibility.

SUMMARY OF THE INVENTION

The present invention provides a novel multistep but straightforward procedure for the quanititative determination of 25-hydroxycholecalciferol which can be applied to animal feed samples with satisfying results.

More particularly the present invention relates to a process for the quantitative determination of 25-hydroxycholecalciferol in animal feed which comprises the steps of
 a) dispersing the feed sample in water and adding to the sample a defined amount of an internal standard compound having a mass different from 25-hydroxycholecalciferol and having a polarity similar to but different from 25-hydroxycholecalciferol;
 b) extracting the aqueous dispersion with tert.butyl methyl ether;
 c) submitting the ether extract to semipreparative HPLC;
 d) collecting the fractions containing 25-hydroxycholecalciferol and the internal standard compound;
 e) submitting the fractions collected in d) or an aliquot thereof to HPLC combined with mass spectrometry;
 f) determining the MS peak areas of 25-hydroxycholecalciferol and of the internal standard compound added; and
 g) calculating the amount of 25-hydroxycholecalciferol by computing the MS peak areas measured.

DETAILED DESCRIPTION OF THE INVENTION

Figure 1:
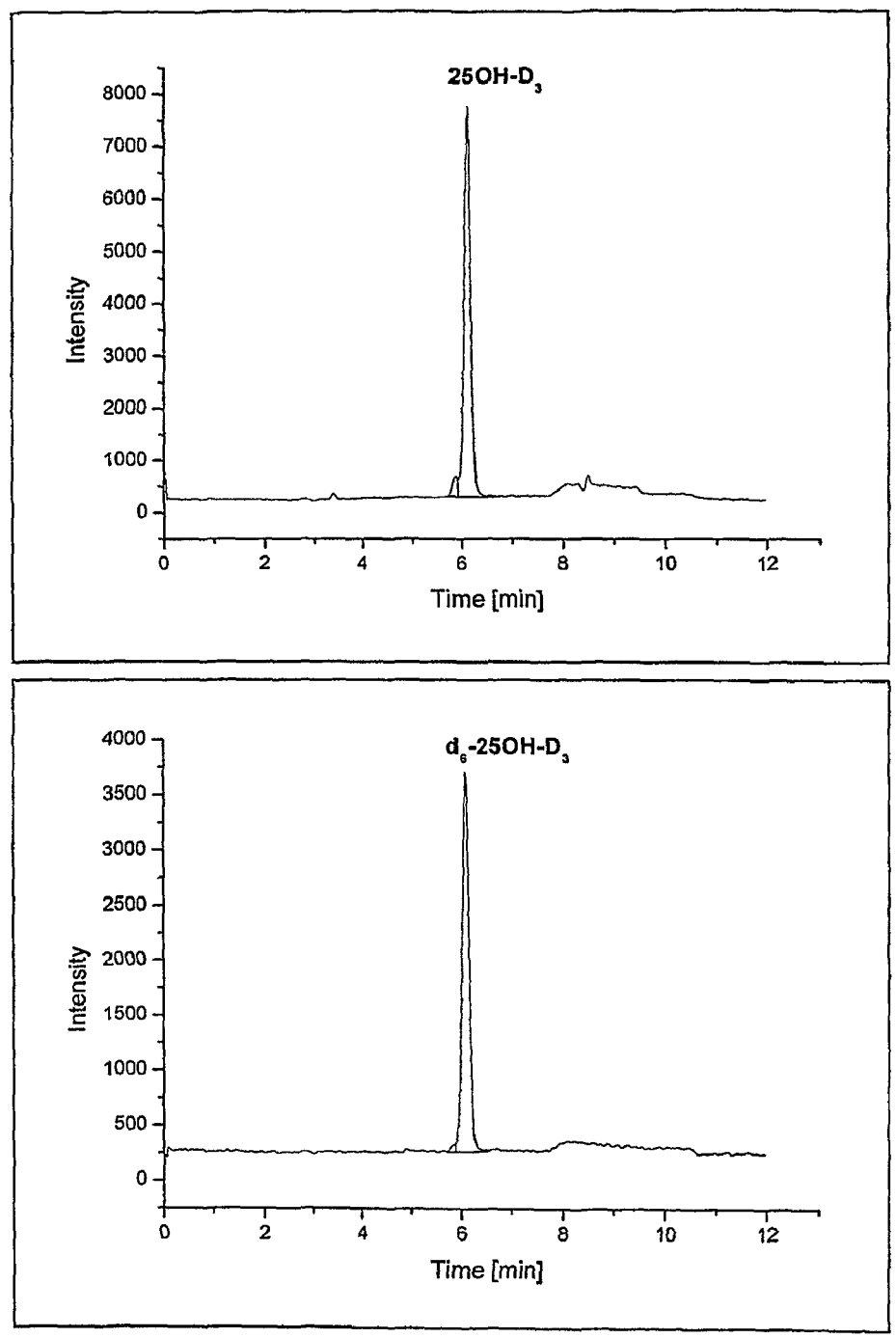
FIG. 1 shows extracted ion chromatograms of the standard solution.

The internal standard compound used in step a) is, e.g., a derivative of, an isomer of or isotopically labeled 25-hydroxycholecalciferol, e.g. a deuterium labeled isotope such as 26,27-hexadeutero-25-hydroxycholecalciferol (Tetrahedron Lett. Vol. 32, No. 24, 2813-2816 (1991); or 25-hydroxyergocalciferol, or 1α-hydroxycholecalciferol. The preferred standard compound is 26,27-hexadeutero-25-hydroxycholecalciferol. The standard compound is suitably added as solution in methanol prior to dispersion or solution of the feed sample in water. The amount of standard compound to be added to the sample is not narrowly critical. Suitably, the standard compound is added in an amount to provide an about 0.05 m to about equimolar concentration based on 25-hydroxycholecalciferol. The aqueous dispersion or solution of the feed sample is then extracted in step b) with an about 1-10 fold mount of tert.butyl methyl ether, preferably with sonication. Semipreparative HPLC in accordance with step c) is accomplished by evaporating the organic solvent from the extract obtained in step b), suitably under exclusion of oxygen, on silica gel using an apolar solvent such as an aliphatic $C_5$-$C_8$ hydrocarbon, e.g., isooctane or mixtures of such solvents with other polar solvents, such as lower alkanols, e.g., isopropanol and/or esters, e.g. ethyl acetate. A preferred system for semipreparative HPLC is silica gel and an isopropanol:ethyl acetate:isooctane mixture of about 1:10:89 (by volume). Analytical HPLC acording to step e) is suitably carried out on a column of an apolar stationary phase such as modified silica gel using a polar solvent such as water or a lower alkanol. The term "modified silica gel" as used herein denotes a reversed-phase silica gel, e.g. silica gel etherified with a $C_{18}$ hydrocarbon moiety, e.g., Aquasil C18 as supplied by Thermo Hypersil-Keystone, Runcom, UK.

The amount of 25-hydroxycholecalciferol in the sample on the basis of the mass spectrometry measurings according to step g) is calculated by the equations shown below:

$$\mu g\ 25\text{-hydroxycholecalciferol}/kg = \frac{Area_{HD}}{Area_{ISD}} * ng\ ISD * RRF * \frac{1}{Weight\ [g]}$$

$$RRF = \text{relative response factor} = \left[\frac{RF_{HD}}{RF_{ISD}}\right] = \left[\frac{Area_{HD}*c_{ISD}}{Area_{ISD}*c_{HD}}\right]$$

$RF$ = Response Factor; $RRF$ = Relative Response Factor;

$ISD$ = Internal Standard Solution; $HD$ = 25-hydroxycholecalcifeol $c$ = concentration [ng/ml].

The relative response factor (RRF) is determined using a solution of both 25-hydroxy-cholecalciferol and 26,27-hexadeutero-25-hydroxycholecalciferol at approx. 5 ng/ml in a solution of methanol:water (70:30).

The invention is illustrated further be the following Example:

EXAMPLE

A. Extraction: 10 g of a feed sample (comprising a mixture of 28.6% Soya, 3% fish meal, 2% Soya oil, 57.3% maize, 2% maize starch, 2% lignosulfonate, 3.1% rice, 2% mineral mix) were weighed into a Erlenmeyer flask. Approx. 500 ng of 26,27-hexadeutero-25-hydroxycholeciferol (0.01 ml of a solution of 2.5 mg 26,27-hexadeutero-25-hydroxycholecalciferol in 50 ml of methanol) and 60 ml of water were added thereto and the slurry was treated in a sonication bath at 50° C. for 10 min. Then, 40 ml of tert.butyl methyl ether were added, the mixture was vigorously shaken for 5 min. and sonicated again for 5 min and centrifuged. 10 ml of the organic supernatant was separated and evaporated under the exclusion of oxygen.

B. Semipreparative HPLC: The residue was dissolved in 2 ml of mobile phase, isopropanol:ethyl acetate:isooctane (1:10:89), centrifuged and an 100 µl aliquot from the clear supernatant was injected into a semipreparative HPLC column of Hypersil Si 60, 3 µm, 120 Å, 150×4.6 mm, (Shandon). The flow rate was 1.0 ml/min. Fractions between 14-16 minutes were collected (fraction separation was checked by injection of mixed standard solution prior to start) and evaporated in a nitrogen stream at 50° C. The residue was dissolved in 0.7 ml of methanol using a ultrasonic bath. Then, 0.3 ml of water were added and the solution injected into an analytical HPLC column combined with a mass spectrometer.

C. Analytical HPLC: Analytical HPLC w as carried out by means of a chromatography system combined with a mass specific detector. The chromatography system ahead of the mass specific detector consisted of a trapping column, on which the substances to be measured are concentrated, and the intrinsic analytical column for separation.

Figure 4:
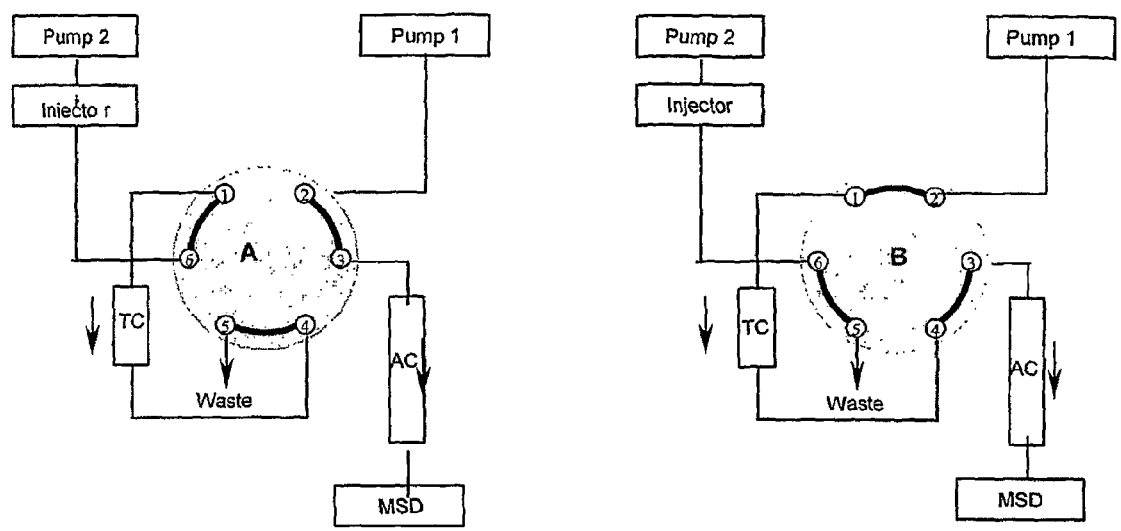
FIG. 4 is a schematical depiction of an installation of the invention.

The installation is schematically depicted in FIG. 4. In FIG. 4, "TC" denotes a trapping column, "AC" denotes an analytical column, and "MSD" denotes the mass specific detector. "A" and "B" symbolize receptacles for the mobile phase of the chromatography system in different modes of operation.

In the trapping column (TC) the stationary phase was Aquasil C18, 3 µm, 2.0×10 mm In the analytical column (AC) the stationary phase was Aquasil C18, 3 µm, 3.0×150 mm. The mobile phase was water (containing 0.05% HCOOH) and a methanol/water (containing 0.05% HCOOH) gradient. The working parameters of the system were as follows:

| | |
|---|---|
| Flow rates: | Pump 1: 0.6 ml/min |
| | Pump 2: 0.7 ml/min |
| Injection volume: | 90 µl |
| Injector temp.: | 5° C. |
| Column temp.: | 40° C. |
| Retention time: | approx. 4 min |

The chromatography was carried out according to the scheme set forth in Table 1 below:

TABLE 1

| Column Switching System | | Trapping Column | | | Analytical Column | | |
|---|---|---|---|---|---|---|---|
| Time | Position | Time | Mobile Phase [1]) | | Time | Mobile Phase [1]) | |
| 0-1.65 | A | 0.00 | 60% B2 | Conditioning | | | |
| | | 0.00-1.00 | >85% B2 | Loading Concentr. | 1-1.65 | 90% B1 | Conditioning |
| | | 1.00-1.65 | 85% B2 | Washing | | | |
| 1.65-2.20 | B | 1.65-2.20 | 90% B1 | Transfer, forward flush | 1.65-2.20 | 90% B1 | Start of chromatography |
| 2.20-12.00 | A | 2.20-2.50 | 85% B2 | Washing | 2.20-6.40 | 90% B1 | Separation |
| | | 2.50-2.60 | >100% B2 | Washing | 6.40-6.50 | >100% | Washing |
| | | 2.60-9.00 | 100% B2 | Washing | 6.50-9.00 | 100% B1 | Washing |
| | | 9.00-9.10 | >60% B2 | | 9.00-9.10 | >90% B1 | Washing, Conditioning |
| | | 9.10-12.0 | 60% B2 | Conditioning | 9.10-12.00 | 90% B1 | Washing, Conditioning |

[1]) > = Gradient (change of the composition of the mobile phase)

The parameters of the mass specific detector (MSD) were as follows:

| | |
|---|---|
| Detector: | Agilent 1946C LC/MSD SL single-quadrupole mass specific detector |
| Ionisation technique: | APCI (atmospheric pressure chemical ionisation |
| Acquisition mode: | SIM (selected ion monitoring) |
| Polarity: | positive |

-continued

| | |
|---|---|
| Spray and drying gas: | Nitrogen 99.999% (quality N50) |
| Drying gas flow: | 9.5 L/min |
| Nebulizer gas pressure: | 50 psig |
| Drying gas temperature: | 225° C. |
| Vaporizer temperature: | 250° C. |
| Capillary voltage: | 3000 V (Vcap = ionisation voltage) |
| Corona current: | 10 μA |
| Gain: | 1.5 |

SIM parameters

| Ion | m/z (M + H)$^+$ | Fragmentor [V] | Dwell time [msec] | rel. Dwell time [%] |
|---|---|---|---|---|
| HyD-H$_2$O | 383.3 | 140 | 226 | 30 |
| d6-HyD-H$_2$O ISD | 389.3 | 140 | 226 | 30 |
| HyD | 401.3 | 90 | 151 | 20 |
| d6-HyD ISD | 407.3 | 90 | 151 | 20 |

Using the above installation and mode of operation, a standard solution, a blank feed sample (no 25-hydroxycholecalciferol present), and a typical feed sample were analyzed. The standard solution was prepared as follows:

1. 25-hydroxycholecalciferol 2.5 mg of 25-Hydroxy vitamin D$_3$ were dissolved in 50 ml of methanol. 2 ml of this solution was diluted to 200 ml with methanol to obtain a solution containing 500 ng/ml.

2. d$_6$-25-hydroxycholecalciferol (internal standard)

2.5 mg of d$_6$-25-hydroxycholecalciferol were dissolved in 50 ml of methanol. 2 ml of this solution was diluted to 200 ml with methanol to obtain a solution containing 500 ng/ml.

3. 1 ml each of the solutions of 25-hydroxycholecalciferol (1.) and d$_6$-25-hydroxycholecalciferol (2.) were diluted to 100 ml with methanol:water (70:30) to obtain a solution containing, per ml, 5 ng of the hydroxylated cholecalciferol.

The blank feed sample was analyzed in analogy to the procedure described in paragraph A. above.

Figure 2:
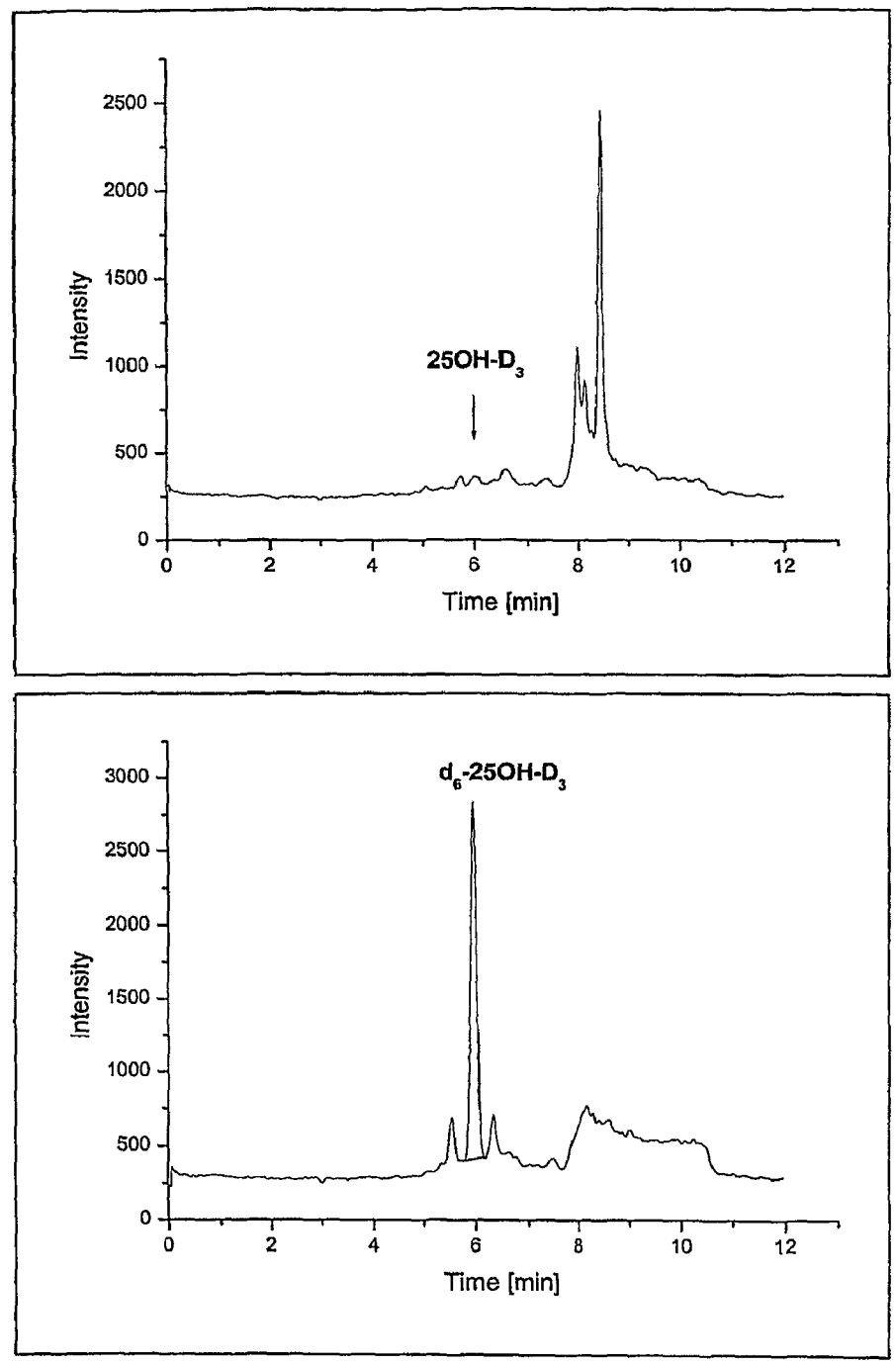
FIG. 2 shows extracted ion chromatograms of the blank feed sample.
Figure 3:
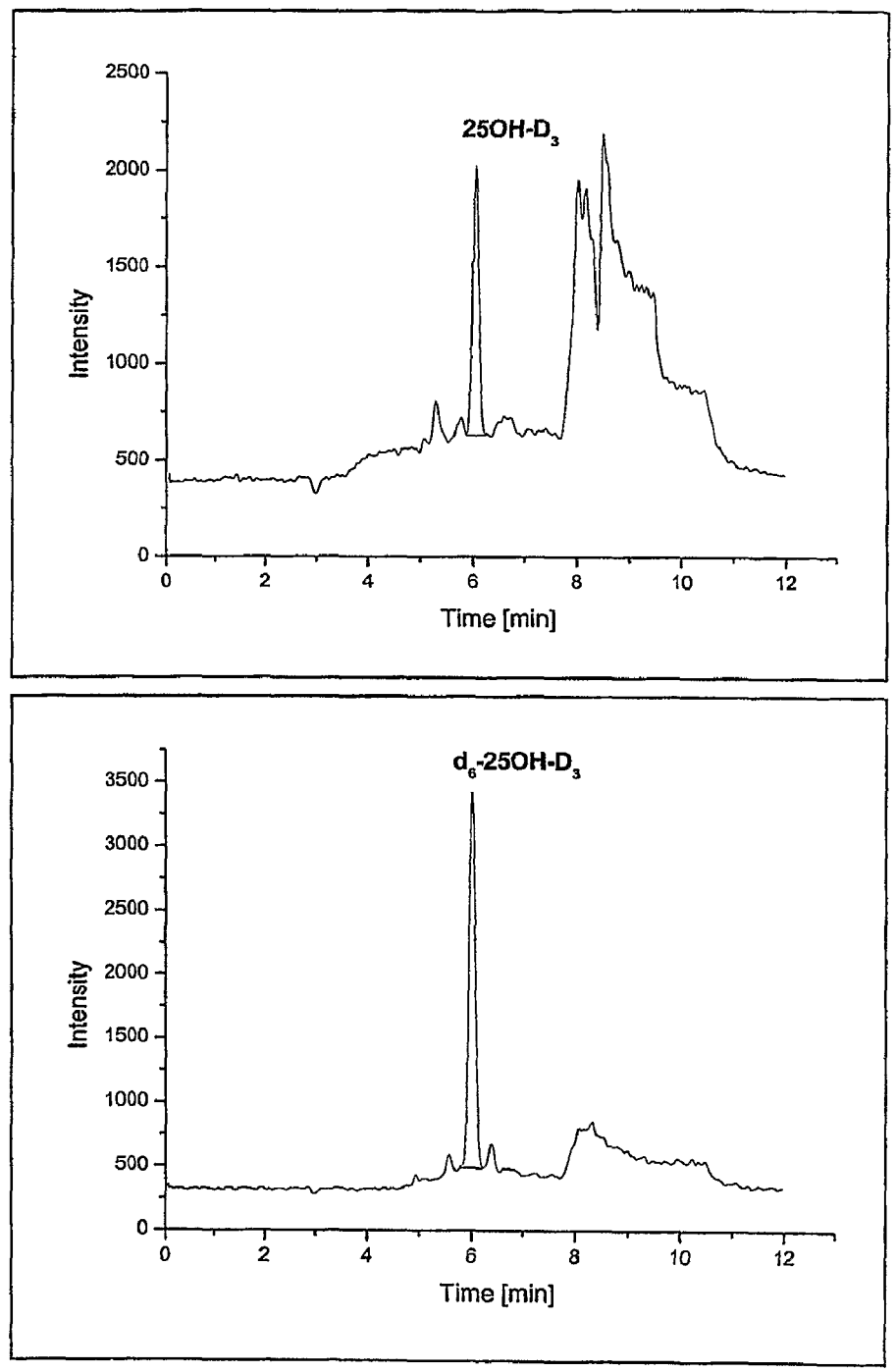
FIG. 3 shows extracted ion chromatograms of a typical feed sample.

The extracted ion chromatograms of the standard solutions, the blank feed sample and the typical feed sample are shown in FIGS. 1-3. The amounts of 25-hydroxycholecalciferol were calculated by the equations given earlier.

What is claimed is:

1. A process for the quantitative determination of 25-hydroxy-cholecalciferol in animal feed which comprises the steps of
   a) dispersing a feed sample in water to form an aqueous dispersion and adding to the sample a defined amount of an internal standard compound hydroxycholecalciferol which is a derivative of, an isomer of, or isotopically labeled 25-hydroxycholecalciferol to obtain an aqueous dispersion;
   b) extracting the aqueous dispersion with tert. butyl methyl ether;
   c) submitting the ether extract to semipreparative HPLC;
   d) collecting fractions containing 25-hydroxycholecalciferol and the internal standard compound;
   e) submitting the fractions collected in d) or an aliquot thereof to HPLC combined with mass speetrometry;
   f) determining MS peak areas of 25-hydroxycholecalciferol and of the internal standard compound added; and
   g) calculating the amount of 25-hydroxycholecalciferol by computing the MS peak areas measured.

2. A process as in claim 1 wherein the standard compound is 26,27-hexadeutero25-hydroxycholecalciferol, 25-hydroxy-ergocalciferol, or 1α-hydroxy-cholecalciferol.

3. A process as in claim 2 wherein the standard compound is 26,27-hexadeutero-25-hydroxycholecalciferol.

4. A process as in claim 1 wherein the semipreparative HPLC is carried out on silica gel as the stationary phase and an isopropanol:ethyl acetate:isooctan mixture as the mobile phase.

5. A process as in claim 4 wherein the mobile phase is isopropanol:ethyl acetate:isooctan in a ratio (by volume) of about 1:10:89.

6. A process as in claim 1 wherein the HPLC of step e) is carried out in a chromatography system comprising a trapping column.

7. A process as in claim 4 wherein the stationary phase in the semipreparative HPLC is a modified silica gel.

8. A process as in claim 6 wherein a gradient of water containing 0.05% (vol/vol) formic acid and methanol containing 0.05% (vol/vol) formic acid is used as the mobile phase.

* * * * *